(12) United States Patent
Ukai et al.

(10) Patent No.: US 11,602,472 B2
(45) Date of Patent: Mar. 14, 2023

(54) HYDROGEN-CONTAINING GAS SUPPLY SYSTEM AND HYDROGEN HOUSE

(71) Applicant: Panasonic Intellectual Property Management Co., Ltd., Osaka (JP)

(72) Inventors: Kunihiro Ukai, Nara (JP); Kazuhito Hato, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 522 days.

(21) Appl. No.: 16/789,843

(22) Filed: Feb. 13, 2020

(65) Prior Publication Data

US 2020/0179205 A1 Jun. 11, 2020

Related U.S. Application Data

(63) Continuation of application No. PCT/JP2018/028524, filed on Jul. 31, 2018.

(30) Foreign Application Priority Data

Sep. 29, 2017 (JP) .............................. JP2017-191506

(51) Int. Cl.
*A61G 10/02* (2006.01)
*A61H 33/14* (2006.01)
(Continued)

(52) U.S. Cl.
CPC .............. *A61G 10/02* (2013.01); *A61H 33/14* (2013.01); *A61M 16/10* (2013.01); *F24F 11/63* (2018.01);
(Continued)

(58) Field of Classification Search
CPC ....... A61H 2033/148; A61G 10/00–04; A61M 21/00–02; A61M 16/10–186
See application file for complete search history.

(56) References Cited

U.S. PATENT DOCUMENTS

2004/0126888 A1 7/2004 Puri
2010/0006099 A1 1/2010 Murota
(Continued)

FOREIGN PATENT DOCUMENTS

CN 101516317 A 8/2009
JP 2016-023833 2/2016
(Continued)

OTHER PUBLICATIONS

English Translation of Chinese Search Report dated Nov. 1, 2021 for the related Chinese Patent Application No. 201880031595.3.
(Continued)

*Primary Examiner* — Thaddeus B Cox
(74) *Attorney, Agent, or Firm* — McDermott Will & Emery LLP

(57) ABSTRACT

A hydrogen-containing gas supply system includes one or more hydrogen-containing gas suppliers, one or more acquirers, and a controller. The one or more hydrogen-containing gas suppliers supply a hydrogen-containing gas to one or more areas in a building. The one or more acquirers acquire information indicating that a person is present in the one or more areas. When it is determined that a person is present in a certain area of the one or more areas in accordance with the information acquired by the acquirers, the controller causes at least one of the one or more hydrogen-containing gas suppliers to supply the hydrogen-containing gas to the certain area.

11 Claims, 10 Drawing Sheets

(51) Int. Cl.
*A61M 16/10* (2006.01)
*F24F 11/63* (2018.01)

(52) U.S. Cl.
CPC .................. *A61H 2033/148* (2013.01); *A61M 2205/588* (2013.01); *A61M 2230/50* (2013.01)

(56) References Cited

U.S. PATENT DOCUMENTS

| | | | | |
|---|---|---|---|---|
| 2011/0225992 | A1* | 9/2011 | Lee ........................... | F24F 1/56 |
| | | | | 62/236 |
| 2019/0285307 | A1* | 9/2019 | Sugiyama ................ | F24F 11/65 |
| 2020/0395122 | A1* | 12/2020 | Takehara ............. | A61M 11/042 |

FOREIGN PATENT DOCUMENTS

| | | |
|---|---|---|
| JP | 2016-114260 | 6/2016 |
| JP | 2017-003190 | 1/2017 |
| JP | 2017-023664 | 2/2017 |
| JP | 2017-086839 | 5/2017 |
| WO | 2008/013163 | 1/2008 |

OTHER PUBLICATIONS

International Search Report of PCT application No. PCT/JP2018/028524 dated Nov. 6, 2018.

\* cited by examiner

HYDROGEN-CONTAINING GAS SUPPLY SYSTEM AND HYDROGEN HOUSE

BACKGROUND

1. Technical Field

The present disclosure relates to a hydrogen-containing gas supply system and a hydrogen house.

2. Description of the Related Art

The reduction effect of hydrogen against the active oxygen and free radicals in the body has recently been attracting attention. For example, treatment for curing a disease or improving a pathological symptom by letting a patient drink hydrogen-containing water, receive an injection of hydrogen-containing water, or inhale a hydrogen-containing gas to reduce the active oxygen and free radicals has been studied at medical institutions.

In addition, development of home devices for readily providing the reduction effect of hydrogen against the active oxygen and free radicals in the body is underway.

For example, there has been proposed a device enabling hydrogen gas stored in a cartridge to be inhaled with an inhaling pipe (see, for example, Japanese Unexamined Patent Application Publication No. 2017-23664).

In addition, there has been proposed a healthful bed device configured to blow out hydrogen gas generated by a hydrogen gas generator from a plurality of holes formed in a bedstead of the bed to increase an intake of hydrogen to the body (see, for example, Japanese Unexamined Patent Application Publication No. 2017-86839).

SUMMARY

However, suppressing, without using an inhaling tool such as an inhaling pipe, an increase in an amount of hydrogen used is not sufficiently studied in the examples of the related art.

One non-limiting and exemplary embodiment provides a hydrogen-containing gas supply system capable of producing a hydrogen inhale effect stably for a long period while suppressing an increase in an amount of hydrogen used, compared with the related art.

In one general aspect, the techniques disclosed here feature a hydrogen-containing gas supply system including one or more hydrogen-containing gas suppliers, one or more acquirers, and a controller. The one or more hydrogen-containing gas suppliers supply a hydrogen-containing gas to one or more areas in a building. The one or more acquirers acquire information indicating that a person is present in the one or more areas. When it is determined that a person is present in a certain area of the one or more areas in accordance with the information acquired by the acquirers, the controller causes at least one of the one or more hydrogen-containing gas suppliers to supply the hydrogen-containing gas to the certain area.

The hydrogen-containing gas supply system according to the aspect of the present disclosure is capable of effectively producing a hydrogen inhale effect stably for a long period while suppressing an increase in an amount of hydrogen used, compared with the related art.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
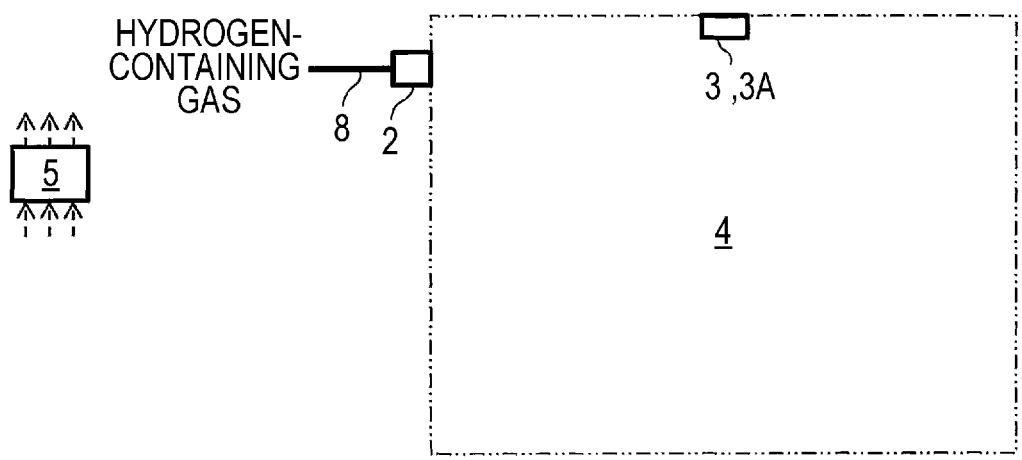
FIG. 1 is a diagram illustrating an example of a hydrogen-containing gas supply system according to a first embodiment.

As described above, examples of methods of taking hydrogen into the body include a method of drinking a hydrogen-dissolved liquid and a method of inhaling a hydrogen-containing gas.

The latter method of inhaling a hydrogen-containing gas enables the inhaled hydrogen to directly dissolve in blood in the lungs, and thus enables the hydrogen to be effectively delivered throughout the body by a blood flow. This case, however, requires a large amount of hydrogen to be supplied in accordance with the respiratory volume, raising a concern about an increase in an amount of hydrogen used.

In light of the above, the amount of hydrogen used can be decreased by using a method of inhaling hydrogen by using an inhaling pipe as in Japanese Unexamined Patent Application Publication No. 2017-23664, for example. The hydrogen inhaling method of Japanese Unexamined Patent Application Publication No. 2017-23664, however, requires an inhaling tool such as the inhaling pipe and still has a room for improvement to allow a person to inhale hydrogen stably for a long period.

Accordingly, a hydrogen-containing gas supply system according to a first aspect of the present disclosure includes one or more hydrogen-containing gas suppliers that supply a hydrogen-containing gas to one or more areas in a building; one or more acquirers that acquire information indicating that a person is present in the one or more areas; and a controller that causes, when it is determined that a person is present in a certain area of the one or more areas in accordance with the information acquired by the acquirers, at least one of the one or more hydrogen-containing gas suppliers to supply the hydrogen-containing gas to the certain area.

In addition, a hydrogen house according to an aspect of the present disclosure includes the hydrogen-containing gas supply system described above.

Such a configuration allows the hydrogen-containing gas supply system and the hydrogen house according to the aspects to produce a hydrogen inhale effect stably for a long period while suppressing an increase in an amount of hydrogen used, compared with the related art. Specifically, when it is determined that a person is present in a certain area of the one or more areas in accordance with the information acquired by the acquirers, the operation of the hydrogen-containing gas supplier is controlled to supply the hydrogen-containing gas to the certain area. Therefore, the hydrogen-containing gas is successfully supplied to the certain area in the building timely. Consequently, an increase in an amount of hydrogen used is successfully suppressed, compared with the case where such hydrogen-containing gas supply control is not performed. In addition, a hydrogen inhale effect is successfully produced stably for a long period compared with the disclosure in Japanese Unexamined Patent Application Publication No. 2017-23664.

A hydrogen-containing gas supply system according to a second aspect of the present disclosure is the hydrogen-containing gas supply system according to the first aspect, wherein the acquirers may be disposed in the areas.

In the case where the acquirers are, for example, motion detectors, by disposing the acquirers at appropriate places in the areas in the building, the acquirers are capable of acquiring a signal indicating detection of presence of a person when the person enters the respective areas in the building.

A hydrogen-containing gas supply system according to a third aspect of the present disclosure is the hydrogen-containing gas supply system according to the first aspect, wherein the controller may cause at least one of the one or more hydrogen-containing gas suppliers to supply the hydrogen-containing gas to the certain area when it is determined that a person is present in the certain area in accordance with the information acquired by the acquirers from an information terminal.

In the case where the acquirers are, for example, receivers that receive information indicating presence of a person from an external information terminal, the acquirers are capable of acquiring schedule information indicating presence of a person in the certain area, such as expected return home time, from the information terminal.

A hydrogen-containing gas supply system according to a fourth aspect of the present disclosure is the hydrogen-containing gas supply system according to the first or second aspect, wherein the one or more hydrogen-containing gas suppliers may be a plurality of hydrogen-containing gas suppliers each of which supplies the hydrogen-containing gas to a corresponding one of a plurality of areas, the one or more acquirers may be a plurality of acquirers each disposed in a corresponding one of the plurality of areas, and the controller may cause, when a certain acquirer among the plurality of acquirers acquires information indicating that a person is present in the certain area and when it is determined that the person is present in the certain area in accordance with the information acquired by the certain acquirer, at least one of the one or more hydrogen-containing gas suppliers to supply the hydrogen-containing gas to the certain area.

Such a configuration allows the acquirers in the hydrogen-containing gas supply system according to the aspect to acquire information for identifying an area where a person is present from among the plurality of areas. Since a hydrogen-containing gas supplier required for an operation of supplying the hydrogen-containing gas is appropriately selectable from among the plurality of hydrogen-containing gas suppliers on the basis of such information, an increase in an amount of hydrogen-containing gas is successfully suppressed.

A hydrogen-containing gas supply system according to a fifth aspect of the present disclosure is the hydrogen-containing gas supply system according to the first or fourth aspect, wherein each of the acquirers may be a first detector that detects that a person is present in the certain area, and upon the first detector detecting that a person is present in the certain area, the controller may cause the hydrogen-containing gas supplier to operate.

A hydrogen-containing gas supply system according to a sixth aspect of the present disclosure is the hydrogen-containing gas supply system according to the first or fourth aspect, wherein each of the acquirers may be a second detector that detects information indicating a position where a person is present in the certain area, and upon the second detector detecting the information indicating the position where the person is present, the controller may cause at least one of the one or more hydrogen-containing gas suppliers to supply the hydrogen-containing gas toward the position.

Such a configuration allows the hydrogen-containing gas supply system according to the aspect to identify, with the second detector, a position where a person is present when the person enters an area, by disposing the second detector at an appropriate place in the area in the building. Thus, the hydrogen-containing gas can be effectively supplied toward the position where the person is present in the area from the hydrogen-containing gas supplier.

A hydrogen-containing gas supply system according to a seventh aspect of the present disclosure is the hydrogen-containing gas supply system according to the first or fourth aspect, wherein each of the acquirers may be a second detector that detects a position where a person is present in the certain area, and the controller may cause at least one of the one or more hydrogen-containing gas suppliers to control at least one of a supply flow rate or a supply flow velocity of the hydrogen-containing gas in accordance with the position where the person is present and that is detected by the second detector.

Such a configuration allows the hydrogen-containing gas supply system according to the aspect to effectively supply the hydrogen-containing gas toward the position where the person is present in the area by controlling at least one of the supply flow rate or the supply flow velocity of the hydrogen-containing gas supplied to the area from the hydrogen-containing gas supplier, in accordance with the position where the person is present and that is detected by the second detector.

For example, when a person is present at a position far from the hydrogen-containing gas supplier, at least one of the supply flow rate or the supply flow velocity of the hydrogen-containing gas may be increased, compared with the case where a person is present at a position near the hydrogen-containing gas supplier. In this way, the hydrogen-containing gas can be effectively supplied to a person at a far position.

A hydrogen-containing gas supply system according to an eighth aspect of the present disclosure is the hydrogen-containing gas supply system according to any one of the first to seventh aspects, wherein the acquirers may further acquire biological information of the person who is present in the certain area, and the controller may cause at least one of the one or more hydrogen-containing gas suppliers to control at least one of a supply flow rate or a supply flow velocity of the hydrogen-containing gas supplied in accordance with the biological information of the person acquired by the acquirers.

Such a configuration allows the hydrogen-containing gas supply system according to the aspect to appropriately control at least one of the supply flow rate or the supply flow velocity of the hydrogen-containing gas supplied to the area from the hydrogen-containing gas supplier on the basis of the biological information of the person acquired by the acquirer.

For example, it is expected that the higher the body temperature serving as the biological information, the more the generated active oxygen and free radicals in the body. Therefore, in this case, an intake of hydrogen into the body is successfully increased as a result of increasing at least one of the supply flow rate or the supply flow velocity of the hydrogen-containing gas supplied to the area from the hydrogen-containing gas supplier. In this way, the reduction effect of hydrogen against the active oxygen and free radicals in the body is successfully increased.

When the body temperature is low, a situation is expected in which an amount of activity is low and generation of the active oxygen and free radicals in the body is low such as during sleeping, for example. Therefore, in this case, an increase in an amount of hydrogen-containing gas is successfully suppressed by decreasing the supply amount of the hydrogen-containing gas supplied to the area from the hydrogen-containing gas supplier.

A hydrogen-containing gas supply system according to a ninth aspect of the present disclosure is the hydrogen-containing gas supply system according to any one of the first to seventh aspects that may further include a hydrogen-containing gas generator that generates the hydrogen-containing gas, wherein the acquirers may further acquire biological information of the person who is present in the certain area, and the controller may control a hydrogen concentration of the hydrogen-containing gas generated by the hydrogen-containing gas generator in accordance with the biological information of the person acquired by the acquirers.

Such a configuration allows the hydrogen-containing gas supply system according to the aspect to appropriately control the hydrogen concentration of the hydrogen-containing gas generated by the hydrogen-containing gas generator in accordance with the biological information of the person acquired by the acquirers.

For example, it is expected that the higher the body temperature serving as the biological information, the more the generated active oxygen and free radicals in the body. Therefore, in this case, an intake of hydrogen into the body is successfully increased as a result of increasing the hydrogen concentration of the hydrogen-containing gas supplied to the area from the hydrogen-containing gas supplier. In this way, the reduction effect of hydrogen against the active oxygen and free radicals in the body is successfully increased.

When the body temperature is low, a situation is expected in which an amount of activity is low and generation of the active oxygen and free radicals in the body is low such as during sleeping, for example. Therefore, in this case, an increase in an amount of hydrogen in the hydrogen-containing gas is successfully suppressed by decreasing the hydrogen concentration of the hydrogen-containing gas supplied to the area from the hydrogen-containing gas supplier.

A hydrogen-containing gas supply system according to a tenth aspect of the present disclosure is the hydrogen-containing gas supply system according to any one of the first to eighth aspects that may further include a filter that removes impurities in air, and a hydrogen-containing gas generator that generates the hydrogen-containing gas by mixing hydrogen with the air having passed through the filter.

Such a configuration allows the hydrogen-containing gas supply system according to the aspect to appropriately remove impurities in the air to be mixed with hydrogen.

A hydrogen-containing gas supply system according to an eleventh aspect of the present disclosure is the hydrogen-containing gas supply system according to any one of the first to tenth aspects that may further include an odorizer that adds an odor to the hydrogen-containing gas, wherein the hydrogen-containing gas supplier may supply to the certain area the hydrogen-containing gas having passed through the odorizer.

Such a configuration of the hydrogen-containing gas supply system according to the aspect allows a person who is present in the certain area to easily know that the hydrogen-containing gas is being supplied to this area by the olfactory sense.

Specific examples of embodiments will be described below with reference to the accompanying drawings.

Each of the specific examples described below illustrates an example of one of the aspects described above. Thus, the shapes, materials, components, arranged positions and connection forms of the components, and so on mentioned below do not limit each of the aspects described above unless they are described in the claims. In addition, among the components mentioned below, each component not described in the independent claims representing the most generic concepts of the aspects is described as an optional component. Further, a description of components assigned the same reference sign in the drawings is omitted in some cases. Furthermore, the drawings schematically illustrate each of the components for ease of understanding, and thus do not accurately illustrate the shapes, the dimension ratios, and so on in some cases.

In operations, the order of steps or the like may be changed as required. In addition, another known step may be added as required.

First Embodiment

[Configuration of System]

Figure 2:
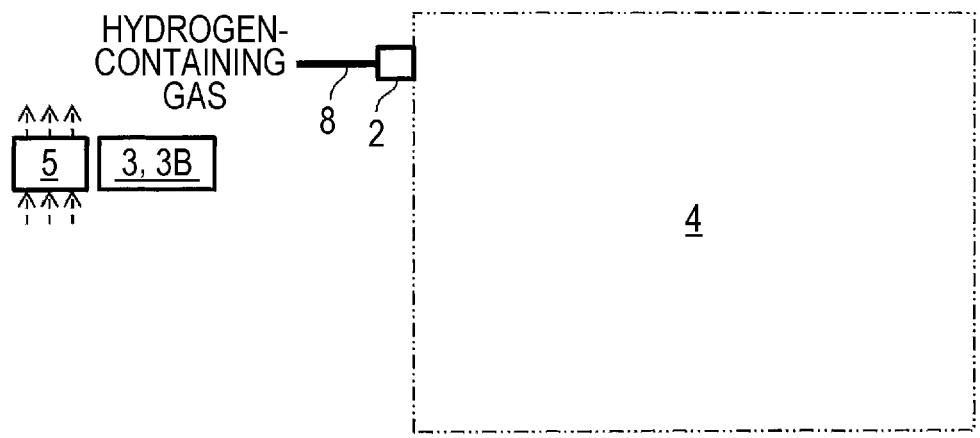
FIG. 2 is a diagram illustrating an example of the hydrogen-containing gas supply system according to the first embodiment.
Figure 3:
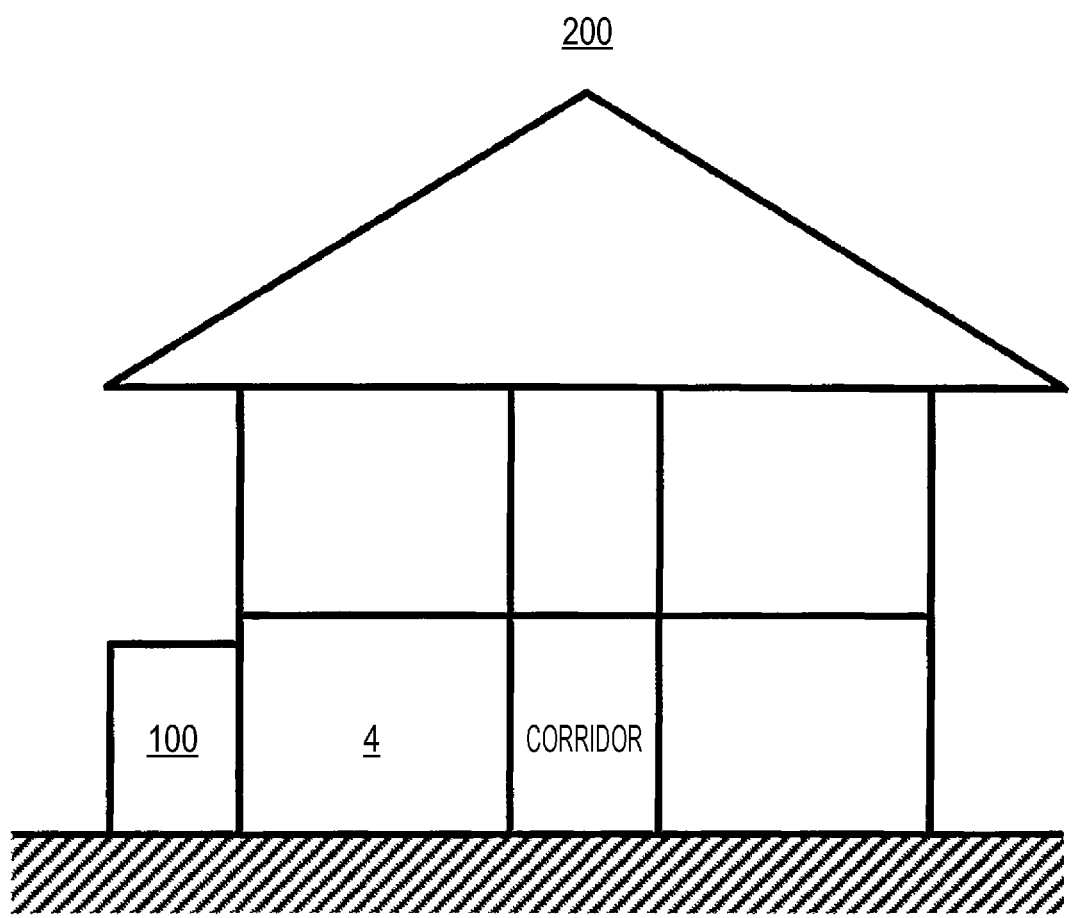
FIG. 3 is a diagram illustrating an example of a hydrogen house according to the first embodiment.

FIGS. 1 and 2 are diagrams each illustrating an example of a hydrogen-containing gas supply system according to a first embodiment. FIG. 3 is a diagram illustrating an example of a hydrogen house according to the first embodiment.

In the example illustrated in FIGS. 1 and 2, a hydrogen-containing gas supply system 100 includes a hydrogen-containing gas supplier 2, an acquirer 3, and a controller 5.

The hydrogen-containing gas supplier 2 is a device that supplies a hydrogen-containing gas to an area 4 in a building.

FIGS. 1 and 2 illustrate only one area 4 in the building. However, when there are a plurality of areas 4 in the building, the hydrogen-containing gas supplier 2 may be provided for each of the areas 4 to supply the hydrogen-containing gas to the corresponding area 4. A configuration in the case where there are the plurality of areas 4 in the building will be described in an example.

In addition, when the building is a hydrogen house 200 (hydrogen home) including the hydrogen-containing gas supply system 100 as illustrated in FIG. 3, for example, a room of the hydrogen house 200, the room constituting the area 4, is equipped with, for example, a door (not illustrated) or the like to a corridor.

The hydrogen-containing gas supplier 2 is disposed, for example, on a wall of the area 4. A hydrogen-containing gas is supplied to the area 4 from the hydrogen-containing gas supplier 2 by using pressure of the hydrogen-containing gas that has passed through a hydrogen-containing gas supply channel 8. In this case, the hydrogen-containing gas supplier 2 is a device that adjusts a flow rate of the hydrogen-containing gas to be supplied to the area 4. The hydrogen-containing gas supplier 2 includes a pressure booster and a flow rate adjusting valve but may include one of these.

For example, an upstream end of the hydrogen-containing gas supply channel 8 that is coupled to the hydrogen-containing gas supplier 2 may be coupled to a hydrogen-containing gas generator (not illustrated in FIGS. 1 and 2). In such a case, a configuration may be adopted in which when the supply pressure of the hydrogen-containing gas from the hydrogen-containing gas generator to the hydrogen-containing gas supplier 2 is low, the flow rate of the hydrogen-containing gas to be supplied to the area 4 is controlled with the aforementioned pressure booster. For example, a fan or the like is usable as the pressure booster but the pressure booster is not limited thereto.

Note that examples of a gas other than hydrogen in the hydrogen-containing gas may include but not limited to air. Hydrogen may be mixed with oxygen gas or nitrogen gas. Details about the case where the hydrogen-containing gas generator generates the hydrogen-containing gas by decreasing the concentration of hydrogen with air will be described in a third embodiment.

In addition, the upstream end of the hydrogen-containing gas supply channel 8 may be coupled to, for example, a high-pressure tank (not illustrated) filled with a high-pressure hydrogen-containing gas. In such a case, a configuration may be adopted in which when the supply pressure of the hydrogen-containing gas is high, the flow rate of the hydrogen-containing gas to be supplied to the area 4 is controlled with the aforementioned flow rate adjusting valve. For example, an electromagnetic valve or the like is usable as the flow rate adjusting valve but the flow rate adjusting valve is not limited thereto.

The acquirer 3 is a device that acquires information indicating that a person is present in the area 4. The acquirer 3 may have any configuration as long as it is capable of acquiring the information indicating that a person is present in the area 4.

An acquirer 3A may be disposed in the area 4 as illustrated in FIG. 1. In this example, the acquirer 3A is disposed on the ceiling of a room constituting the area 4. Note that FIG. 1 illustrates only one area 4 in the building. However, when there are a plurality of areas 4 in the building, the acquirer 3A may be disposed in each of the areas 4. A configuration in the case where there are the plurality of areas 4 in the building will be described in an example.

The acquirer 3A may be a detector that detects that a person is present in the area 4. Examples of such an acquirer 3A may include a motion detector. For example, an infrared sensor is usable as the motion detector but the motion detector is not limited thereto.

When the acquirer 3A is, for example, a motion detector, the "information indicating that a person is present in the area 4" is a detection signal of presence of a person in the area 4. Therefore, by disposing the acquirer 3A at an appropriate place in the area 4 in the building, the acquirer 3A successfully acquires the detection signal of presence of a person in the area 4 when the person enters the area 4 in the building. In addition, when the person exits from the area 4, the acquirer 3A successfully acquires a detection signal of absence of a person in the area 4.

As illustrated in FIG. 2, an acquirer 3B may be disposed outside the area 4. Examples of such an acquirer 3B may include a receiver that receives information indicating presence of a person from an external information terminal not illustrated. In this case, the "information indicating that a person is present in the area 4" is schedule information of presence of a person in the area 4 in the building, such as expected return home time, received from an external information terminal.

The controller 5 causes the hydrogen-containing gas to be supplied to the area 4 from the hydrogen-containing gas supplier 2 when it is determined that a person is present in the area 4 on the basis of the information acquired by the acquirer 3.

For example, upon the acquirer 3A detecting presence of a person in the area 4, the controller 5 may cause the hydrogen-containing gas supplier 2 to operate.

In addition, for example, when it is determined that a person is present in the area 4 on the basis of the information acquired by the acquirer 3B from the information terminal, the controller 5 may cause the hydrogen-containing gas to be supplied to the area 4 from the hydrogen-containing gas supplier 2.

The controller 5 may have any configuration as long as it has a control function. The controller 5 includes, for example, arithmetic circuitry (not illustrated) and storage circuitry (not illustrated) that stores a control program. Examples of the arithmetic circuitry include an MPU, a CPU, and so on. Examples of the storage circuitry include a memory and so on. The controller 5 may be constituted by a single controller that performs centralized control or by a plurality of controllers that operate in cooperation with each other to perform distributed control.

[Operation]

Figure 4:
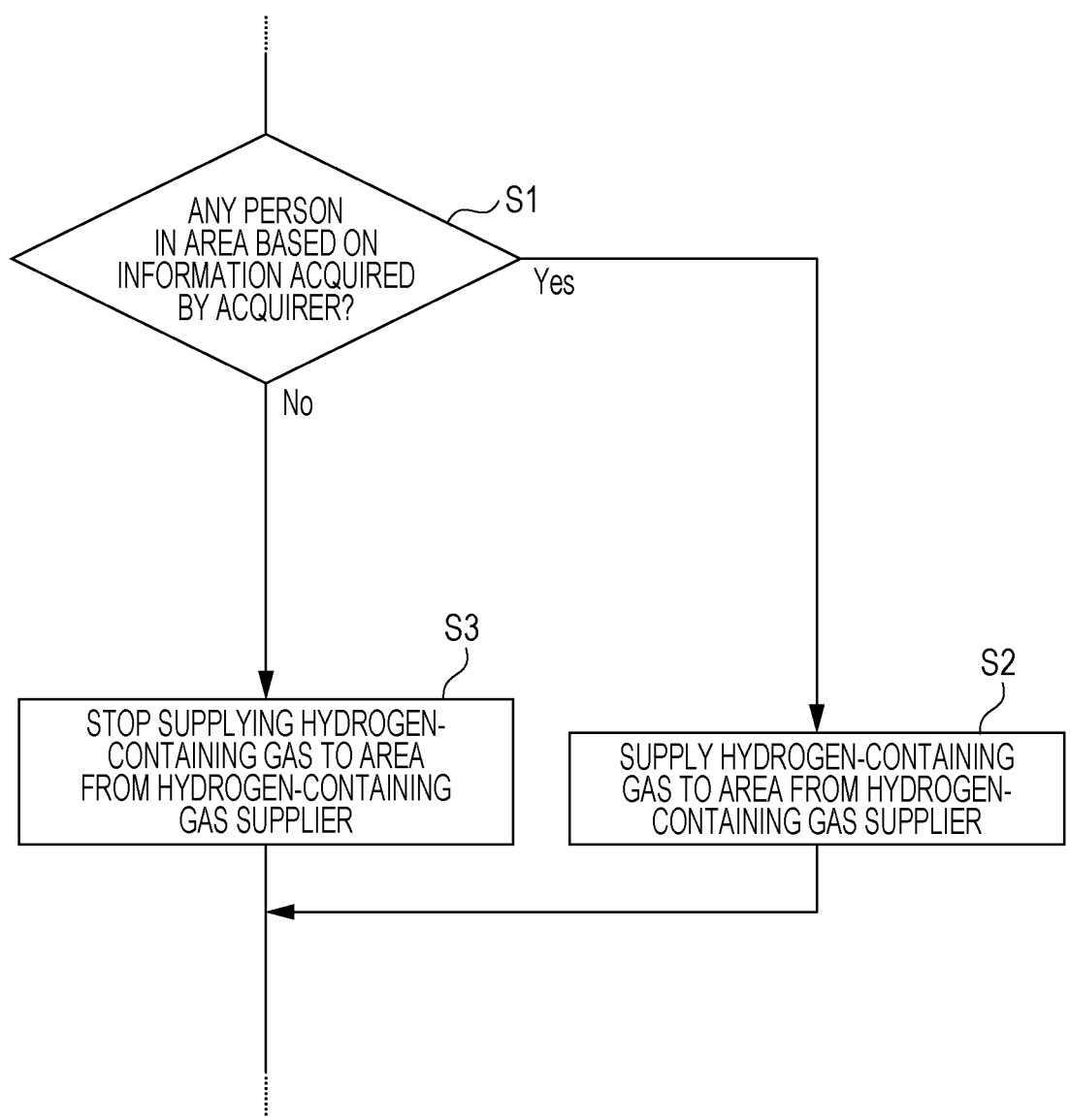
FIG. 4 is a flowchart illustrating an example of an operation of the hydrogen-containing gas supply system according to the first embodiment.

FIG. 4 is a flowchart illustrating an example of an operation of the hydrogen-containing gas supply system according to the first embodiment. The operation described below may be performed by the arithmetic circuitry of the controller 5 in accordance with the control program read from the storage circuitry. However, it is not necessarily mandatory for the controller 5 to perform the operation described below. An operator may perform part or entirety of the operation.

First, the acquirer 3 is caused to start operating so that the acquirer 3 is able to acquire the information indicating that a person is present in the area 4. Note that if the acquirer 3 is, for example, a motion detector such as an infrared sensor, the acquirer 3 may be set to operate all the time because power consumption of the sensor is small.

In this state, it is determined in step S1 whether a person is present in the area 4 on the basis of the information acquired by the acquirer 3.

Here, if the acquirer 3 is, for example, a motion detector such as an infrared sensor disposed in the area 4, it is determined in step S1 whether the motion detector has detected presence of a person who has entered the area 4. That is, the determination in step S1 is made as a result of a detection signal of presence or absence of a person in the area 4 being transmitted from the motion detector to the controller 5.

In addition, if the acquirer 3 is, for example, a receiver, it is determined in step S1 whether a person is present in the area 4 on the basis of schedule information of presence of a person in the area 4, such as expected return home time, received by the receiver from an external information terminal. That is, the determination in step S1 is made as a result of the schedule information of presence of a person in the area 4 being transmitted from the receiver to the controller 5.

If it is determined that a person is present in the area 4 on the basis of the information acquired by the acquirer 3 (if "Yes" in step S1), the hydrogen-containing gas is supplied to the area 4 from the hydrogen-containing gas supplier 2 (step S2). If the operation of the hydrogen-containing gas supplier 2 is stopped in the previous cycle, the operation of the hydrogen-containing gas supplier 2 is started in step S2. If the operation of the hydrogen-containing gas supplier 2 is started in the previous cycle, the state of the hydrogen-containing gas supplier 2 is maintained as it is in step S2. Thereafter, the operation of step S1 and the subsequent steps is repeated from step S1 at a predetermined cycle time.

If the aforementioned schedule information is the expected return home time, supplying of the hydrogen-containing gas to the area 4 from the hydrogen-containing gas supplier 2 may be started when the expected return home time is reached, or supplying of the hydrogen-containing gas to the area 4 from the hydrogen-containing gas supplier 2 may be started before the expected return home time. The latter case allows the hydrogen inhale effect to be quickly exhibited since the area 4 is successfully filled with an appropriate amount of hydrogen-containing gas when a person enters the area 4.

On the other hand, if it is determined that a person is not present in the area 4 on the basis of the information acquired by the acquirer 3 (if "No" in step S1), supplying of the hydrogen-containing gas to the area 4 from the hydrogen-containing gas supplier 2 is stopped (step S3). If the operation of the hydrogen-containing gas supplier 2 is stopped in the previous cycle, the state of the hydrogen-containing gas supplier 2 is maintained as it is in step S3. If the operation of the hydrogen-containing gas supplier 2 is started in the previous cycle, the operation of the hydrogen-containing gas supplier 2 is stopped in step S3. Thereafter, the operation of step S1 and the subsequent steps is repeated from step S1 at the predetermined cycle time.

As described above, the hydrogen-containing gas supply system 100 and the hydrogen house 200 according to the present embodiment is capable of producing a hydrogen inhale effect stably for a long period while suppressing an increase in an amount of hydrogen used, compared with the related art.

Specifically, when it is determined that a person is present in the area 4 on the basis of the information acquired by the acquirer 3, the operation of the hydrogen-containing gas supplier 2 is controlled to supply the hydrogen-containing gas to the area 4. Therefore, the hydrogen-containing gas is successfully supplied to the area 4 in the building timely. Consequently, an increase in an amount of hydrogen used is successfully suppressed, compared with the case where such hydrogen-containing gas supply control is not performed. In addition, a hydrogen inhale effect is successfully produced stably for a long period compared with the disclosure in Japanese Unexamined Patent Application Publication No. 2017-23664.

Further, when it is determined that a person is not present in the area 4 on the basis of the information acquired by the acquirer 3, the operation of the hydrogen-containing gas supplier 2 is controlled to stop supplying of the hydrogen-containing gas to the area 4. Therefore, an increase in an amount of hydrogen used is successfully suppressed, compared with the case where such hydrogen-containing gas supply stop control is not performed.

Example

[Configuration of System]

Figure 5:
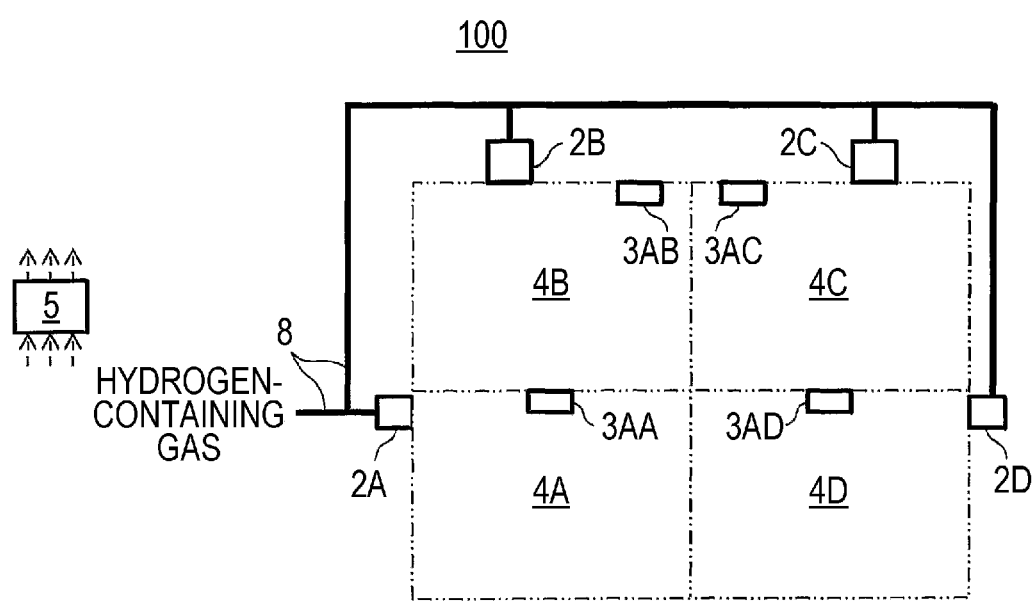
FIG. 5 is a diagram illustrating an example of the hydrogen-containing gas supply system according to an example of the first embodiment.

FIG. 5 is a diagram illustrating an example of a hydrogen-containing gas supply system according to an example of the first embodiment.

In the example illustrated in FIG. 5, the hydrogen-containing gas supply system 100 includes hydrogen-containing gas suppliers 2A, 2B, 2C, and 2D; acquirers 3AA, 3AB, 3AC, and 3AD; and the controller 5.

Here, the hydrogen-containing gas suppliers 2A, 2B, 2C, and 2D are four hydrogen-containing gas suppliers that supply a hydrogen-containing gas to a plurality of areas 4A, 4B, 4C, and 4D, respectively.

The hydrogen-containing gas suppliers 2A, 2B, 2C, and 2D are substantially the same as the hydrogen-containing gas supplier 2 according to the first embodiment except for the point mentioned above. Thus, a detailed description is omitted.

In addition, the acquirers 3AA, 3AB, 3AC, and 3AD are four acquirers disposed in the plurality of areas 4A, 4B, 4C, and 4D, respectively.

The acquirers 3AA, 3AB, 3AC, and 3AD are substantially the same as the acquirer 3A according to the first embodiment except for the point mentioned above. Thus, a detailed description is omitted.

Note that when the building is the hydrogen house 200, rooms such as bedrooms in the hydrogen house 200 constitute the respective areas 4A, 4B, 4C, and 4D. In this case, there are a corridor not illustrated and doors, not illustrated, to the corridor between the areas 4A, 4B, 4C, and 4D.

The number of hydrogen-containing gas suppliers 2A, 2B, 2C, and 2D, the number of areas 4A, 4B, 4C, and 4D, and the number of acquirers 3AA, 3AB, 3AC, and 3AD mentioned above are merely examples and are not limited to these examples.

When a certain acquirer among the acquirers 3AA, 3AB, 3AC, and 3AD acquires information indicating that a person is present in a certain area and when it is determined that a person is present in the certain area on the basis of the information acquired by the certain acquirer, the controller 5 causes the hydrogen-containing gas to be supplied to the certain area from the hydrogen-containing gas supplier that supplies the hydrogen-containing gas to this certain area.

The controller 5 may be substantially the same as the controller 5 according to the first embodiment except for the point mentioned above.

[Operation]

Figure 6:
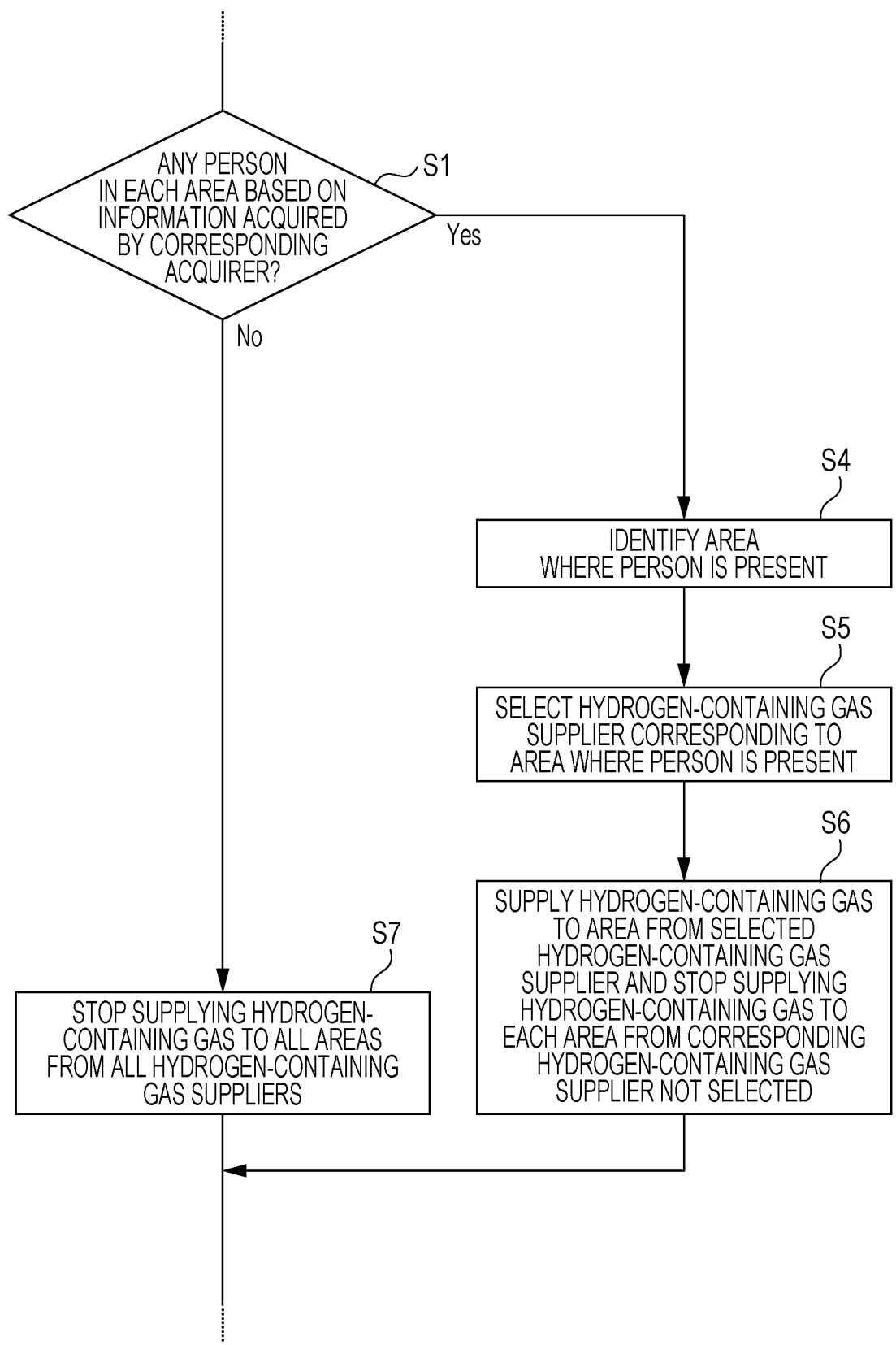
FIG. 6 is a flowchart illustrating an example of an operation of the hydrogen-containing gas supply system according to the example of the first embodiment.

FIG. 6 is a flowchart illustrating an example of an operation of the hydrogen-containing gas supply system according to the example of the first embodiment. The operation described below may be performed by the arithmetic circuitry of the controller 5 in accordance with the control program read from the storage circuitry. However, it is not necessarily mandatory for the controller 5 to perform the operation described below. An operator may perform part or entirety of the operation. Since step S1 of FIG. 6 is substantially the same as step S1 of FIG. 4, a detailed description is omitted.

If it is determined that a person is present in any of the areas 4A, 4B, 4C, and 4D on the basis of the information acquired by the acquirers 3AA, 3AB, 3AC, and 3AD (if "Yes" in step S1), the area where the person is present is identified (step S4). Note that if there are a plurality of areas where a person is present, the plurality of areas may be identified.

Subsequently, in step S5, the hydrogen-containing gas supplier corresponding to the area identified in step S4 is selected.

Then, in step S6, the hydrogen-containing gas is supplied to the area from the hydrogen-containing gas supplier selected in step S5, and supplying of the hydrogen-containing gas to the areas from the hydrogen-containing gas suppliers not selected in step S5 is stopped. Thereafter, the operation of step S1 and the subsequent steps is repeated from step S1 at a predetermined cycle time.

For example, when it is determined that a person is present in the areas 4A and 4D on the basis of the information acquired from the acquirers 3AA and 3AD, the hydrogen-containing gas is supplied to the areas 4A and 4D from the hydrogen-containing gas suppliers 2A and 2D, respectively, and supplying of the hydrogen-containing gas to the areas 4B and 4C from the hydrogen-containing gas suppliers 2B and 2C, respectively, is stopped in step S6.

In addition, for example, when it is determined that a person is present in the area 4A on the basis of the information acquired by the acquirer 3AA in the previous cycle and when the person moves from the area 4A to the area 4B, the hydrogen-containing gas is supplied to the area 4B from the hydrogen-containing gas supplier 2B and supplying of the hydrogen-containing gas to the area 4A from the hydrogen-containing gas supplier 2A is stopped.

On the other hand, if it is determined that a person is not present in all the areas 4A, 4B, 4C, and 4D on the basis of the information acquired by the acquirers 3AA, 3AB, 3AC, and 3AD (if "No" in step S1), supplying of the hydrogen-containing gas to all the areas 4A, 4B, 4C, and 4D from all the hydrogen-containing gas suppliers 2A, 2B, 2C, and 2D, respectively, is stopped (step S7). Thereafter, the operation of step S1 and the subsequent steps is repeated from step S1 at a predetermined cycle time.

As described above, in the hydrogen-containing gas supply system 100 according to the present example, the acquirers 3AA, 3AB, 3AC, and 3AD are able to acquire information for identifying an area where a person is present from among the areas 4A, 4B, 4C, and 4D. Since a hydrogen-containing gas supplier required for an operation of supplying the hydrogen-containing gas is appropriately selectable from among the hydrogen-containing gas suppliers 2A, 2B, 2C, and 2D on the basis of such information, an increase in an amount of hydrogen-containing gas is successfully suppressed.

The hydrogen-containing gas supply system 100 according to the present example may be substantially the same as the hydrogen-containing gas supply system 100 according to the first embodiment except for the features mentioned above.

Second Embodiment

[Configuration of System]

Figure 7:
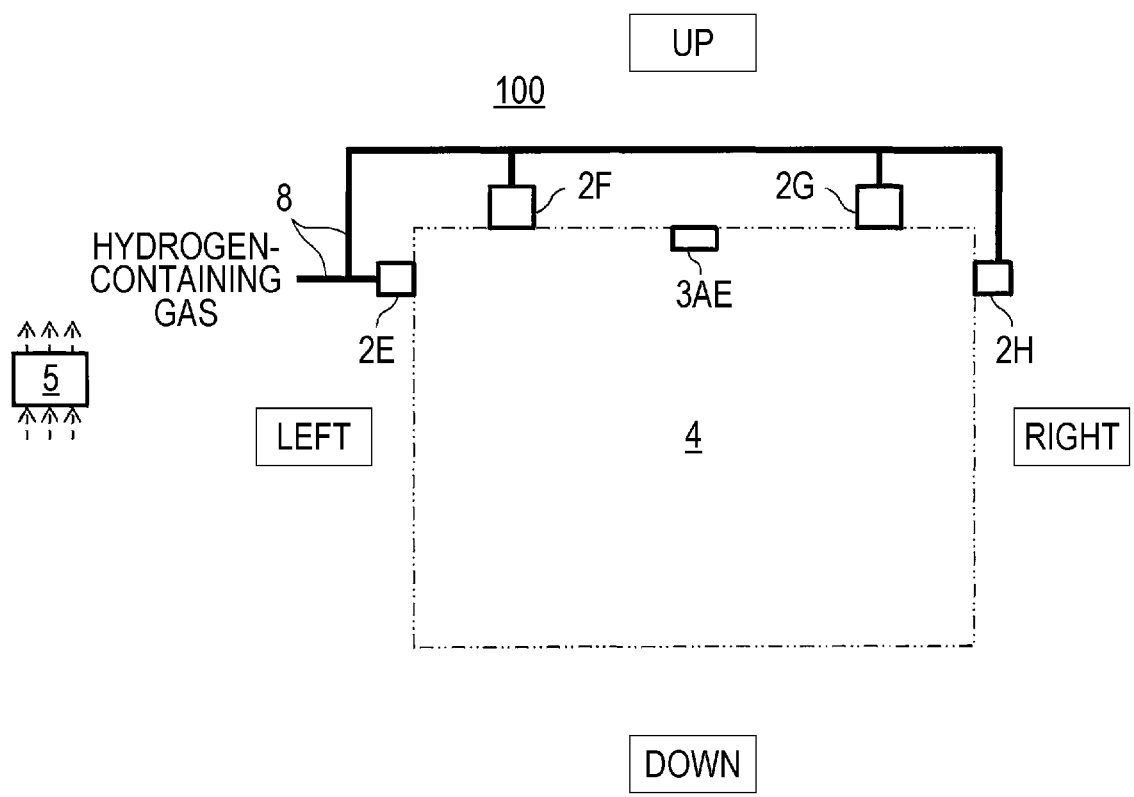
FIG. 7 is a diagram illustrating an example of a hydrogen-containing gas supply system according to a second embodiment.

FIG. 7 is a diagram illustrating an example of a hydrogen-containing gas supply system according to a second embodiment. Note that "UP", "DOWN", "RIGHT", and "LEFT" are set as illustrated in FIG. 7.

In the example illustrated in FIG. 7, the hydrogen-containing gas supply system 100 includes hydrogen-containing gas suppliers 2E, 2F, 2G, and 2H, an acquirer 3AE, and the controller 5.

In this example, the hydrogen-containing gas supplier 2E is disposed in an upper part of a left wall of the area 4. The hydrogen-containing gas supplier 2F is disposed in a left part of an upper wall of the area 4. The hydrogen-containing gas supplier 2G is disposed in a right part of the upper wall of the area 4. The hydrogen-containing gas supplier 2H is disposed in an upper part of a right wall of the area 4.

The hydrogen-containing gas suppliers 2E, 2F, 2G, and 2H are substantially the same as the hydrogen-containing gas supplier 2 according to the first embodiment except for the point mentioned above. Thus, a detailed description is omitted.

Note that the arranged positions of the hydrogen-containing gas suppliers 2E, 2F, 2G, and 2H and the number of hydrogen-containing gas suppliers 2E, 2F, 2G, and 2H are merely examples and are not limited to these examples.

The acquirer 3AE is a detector that detects information indicating a position where a person is present in the area 4. For example, an infrared sensor is usable as such an acquirer 3AE.

The acquirer 3AE may be substantially the same as the acquirer 3A according to the first embodiment except for the point mentioned above.

In addition, although the illustration is omitted, if a person carries an information terminal (smartphone, for example) all the time in the area 4, the position where the person is present in the area 4 may be detected on the basis of position information of such a portable information terminal, instead of using the acquirer 3AE.

Upon the acquirer 3AE detecting information indicating a position where a person is present, the controller 5 causes a hydrogen-containing gas to be supplied toward the position from the hydrogen-containing gas supplier.

The controller 5 may be substantially the same as the controller 5 according to the first embodiment except for the point mentioned above.

[Operation]

Figure 8:
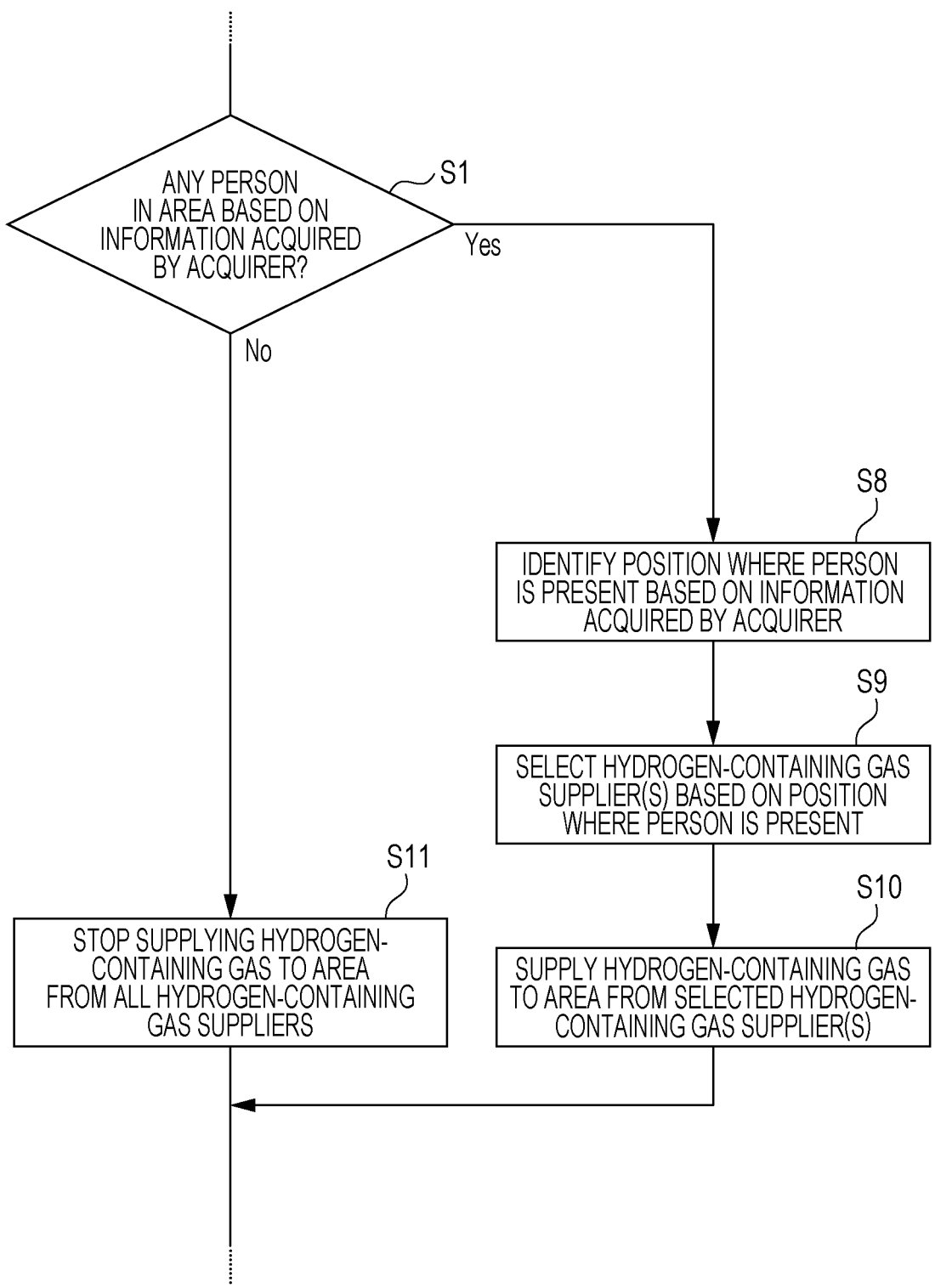
FIG. 8 is a flowchart illustrating an example of an operation of the hydrogen-containing gas supply system according to the second embodiment.

FIG. 8 is a flowchart illustrating an example of an operation of the hydrogen-containing gas supply system according to the second embodiment. The operation described below may be performed by the arithmetic circuitry of the controller 5 in accordance with the control program read from the storage circuitry. However, it is not necessarily mandatory for the controller 5 to perform the operation described below. An operator may perform part or entirety of the operation. Since step S1 of FIG. 8 is substantially the same as step S1 of FIG. 4, a detailed description is omitted.

If it is determined that a person is present in the area 4 on the basis of the information acquired by the acquirer 3AE (if "Yes" in step S1), a position where the person is present is identified on the basis of the information acquired by the acquirer 3AE (step S8).

Subsequently, in step S9, a hydrogen-containing gas supplier required for an operation of supplying the hydrogen-containing gas is appropriately selected from among the hydrogen-containing gas suppliers 2E, 2F, 2G, and 2H on the basis of the position where the person is present and that is identified in step S8.

Then, in step S10, the hydrogen-containing gas is supplied to the area 4 from the hydrogen-containing gas supplier selected in step S9. Thereafter, the operation of step S1 and the subsequent steps is repeated from step S1 at a predetermined cycle time.

For example, when a person is present around the center of the area 4 in FIG. 7, the hydrogen-containing gas suppliers 2F and 2G are selected in step S9 and the hydrogen-containing gas is supplied to the area 4 from the hydrogen-containing gas suppliers 2F and 2G in step S10.

In addition, for example, when a person is present in a right part of the area 4 in FIG. 7, the hydrogen-containing gas suppliers 2G and 2H are selected in step S9 and the hydrogen-containing gas is supplied to the area 4 from the hydrogen-containing gas suppliers 2G and 2H in step S10.

Further, for example, when a person is present in a left part of the area 4 in FIG. 7, the hydrogen-containing gas suppliers 2E and 2F are selected in step S9 and the hydrogen-containing gas is supplied to the area 4 from the hydrogen-containing gas suppliers 2E and 2F in step S10.

On the other hand, if it is determined that a person is not present in the area 4 on the basis of the information acquired by the acquirer 3AE (if "No" in step S1), supplying of the hydrogen-containing gas to the area 4 from all the hydrogen-containing gas suppliers 2E, 2F, 2G, and 2H is stopped (step S11). Thereafter, the operation of step S1 and the subsequent steps is repeated from step S1 at a predetermined cycle time.

As described above, the hydrogen-containing gas supply system 100 according to the present embodiment includes the acquirer 3AE disposed at an appropriate place of the area 4 in the building and thus successfully identifies a position where a person is present by using the acquirer 3AE when the person enters the area 4. Therefore, the hydrogen-containing gas can be effectively supplied toward the position where the person is present in the area 4 from the hydrogen-containing gas supplier.

The hydrogen-containing gas supply system 100 according to the present embodiment may be substantially the same as the hydrogen-containing gas supply system 100 according to the first embodiment or the example of the first embodiment except for the features mentioned above.

(First Modification)

While the method has been described in which the hydrogen-containing gas supply system 100 according to the second embodiment effectively supplies a hydrogen-containing gas toward a position where a person is present in the area 4 by appropriately selecting a hydrogen-containing gas supplier from among the hydrogen-containing gas suppliers 2E, 2F, 2G, and 2H on the basis of the position where the person is present, the method is not limited thereto.

In the hydrogen-containing gas supply system 100 according to the present modification, the controller 5 controls at least one of a supply flow rate or a supply flow velocity of the hydrogen-containing gas supplied to the area 4 from the hydrogen-containing gas supplier in accordance with the position where a person is present and that is detected by the acquirer 3AE. For example, the controller 5 may control a supply amount of hydrogen-containing gas supplied to the area 4 from the hydrogen-containing gas supplier by controlling an operation of a not-illustrated pressure booster (fan, for example) included in the hydrogen-containing gas supplier.

In this way, the hydrogen-containing gas supply system 100 according to the present modification controls at least one of the supply flow rate or the supply flow velocity of the hydrogen-containing gas supplied to the area 4 from the hydrogen-containing gas supplier in accordance with the position where a person is present and that is detected by the acquirer 3AE, thereby being able to effectively supply the hydrogen-containing gas toward the position where the person is present in the area 4.

For example, when a person is present at a position far from the hydrogen-containing gas supplier, at least one of the supply flow rate or the supply flow velocity of the hydrogen-containing gas may be increased, compared with the case where a person is present at a position near the hydrogen-containing gas supplier. In this way, the hydrogen-containing gas can be effectively supplied to a person at a far position.

The hydrogen-containing gas supply system 100 according to the present modification may be substantially the same as the hydrogen-containing gas supply system 100 according to the first embodiment or the example of the first embodiment except for the features mentioned above. That is, the hydrogen-containing gas supply system 100 according to the present modification is not limited to the configuration including the hydrogen-containing gas suppliers 2E, 2F, 2G, and 2H illustrated in FIG. 7, and may have a configuration in which one hydrogen-containing gas supplier 2 is disposed in the area 4 as illustrated in FIG. 1.

(Second Modification)

While the method has been described in which the hydrogen-containing gas supply system 100 according to the second embodiment effectively supplies a hydrogen-containing gas toward a position where a person is present in the area 4 by appropriately selecting a hydrogen-containing gas supplier from among the hydrogen-containing gas suppliers 2E, 2F, 2G, and 2H on the basis of the position where the person is present, the method is not limited thereto.

In the hydrogen-containing gas supply system 100 according to the present modification, the controller 5 changes a direction in which the hydrogen-containing gas is issued to the area 4 to a desired direction in accordance with a position where a person is present and that is detected by the acquirer 3AE, by using a mechanism (not illustrated) capable of changing the direction in which the hydrogen-containing gas is issued such as a louver configuration included in the hydrogen-containing gas supplier.

In this way, the hydrogen-containing gas supply system 100 according to the present modification appropriately controls the direction in which the hydrogen-containing gas is issued in accordance with the position where a person is present and that is detected by the acquirer 3AE, thereby being able to effectively supply the hydrogen-containing gas toward the position where the person is present in the area 4.

The hydrogen-containing gas supply system 100 according to the present modification may be substantially the same as the hydrogen-containing gas supply system 100 according to the first embodiment or the example of the first embodiment except for the features mentioned above. That is, the hydrogen-containing gas supply system 100 according to the present modification is not limited to the configuration including the hydrogen-containing gas suppliers 2E, 2F, 2G, and 2H illustrated in FIG. 7, and may have a configuration in which one hydrogen-containing gas supplier 2 is disposed in the area 4 as illustrated in FIG. 1.

Third Embodiment

[Configuration of System]

Figure 9:
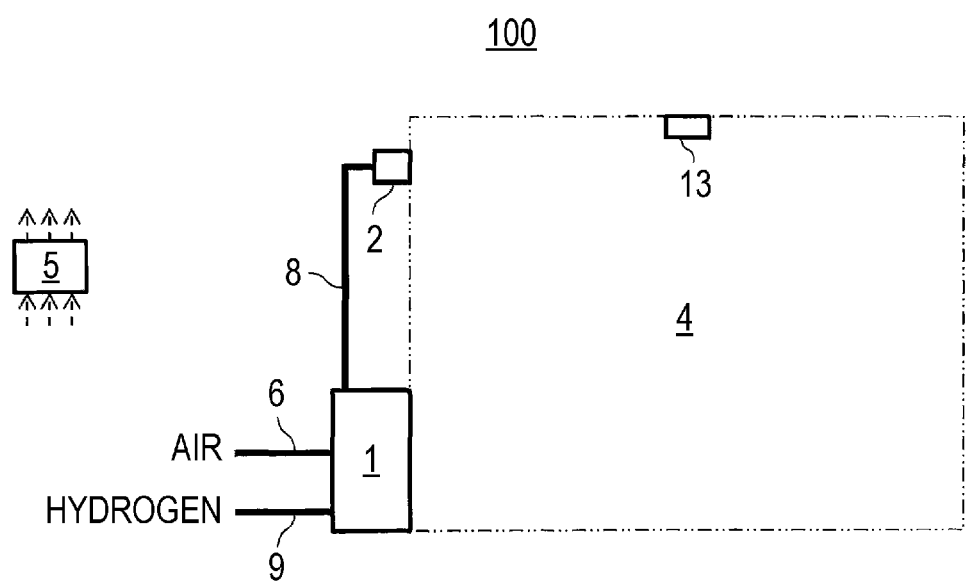
FIG. 9 is a diagram illustrating an example of a hydrogen-containing gas supply system according to a third embodiment.

FIG. 9 is a diagram illustrating an example of a hydrogen-containing gas supply system according to a third embodiment.

In the example illustrated in FIG. 9, the hydrogen-containing gas supply system 100 includes a hydrogen-containing gas generator 1, the hydrogen-containing gas supplier 2, an acquirer 13, and the controller 5. Since the hydrogen-containing gas supplier 2 is substantially the same as that of the first embodiment, a description is omitted.

The hydrogen-containing gas generator 1 is a device that generates a hydrogen-containing gas. The hydrogen-containing gas generator 1 may have any configuration as long as it is capable of generating the hydrogen-containing gas.

For example, an air supply channel 6 for taking in air from the atmosphere and a hydrogen supply channel 9 for taking in hydrogen from a hydrogen source are coupled to the hydrogen-containing gas generator 1 illustrated in FIG. 9. Thus, the hydrogen-containing gas generator 1 is capable of generating a hydrogen-containing gas of a desired hydrogen concentration by mixing hydrogen from the hydrogen supply channel 9 and air from the air supply channel 6 at a predetermined mixing ratio. The hydrogen-containing gas generated by the hydrogen-containing gas generator 1 is supplied to the hydrogen-containing gas supplier 2 through the hydrogen-containing gas supply channel 8.

Note that the hydrogen-containing gas generator 1 may include a buffer tank (not illustrated) for stabilizing a supply amount of hydrogen-containing gas. Examples of the hydrogen source mentioned above may include but not limited to a water electrolysis device or the like. In addition, the hydrogen-containing gas generator 1 may mix hydrogen with oxygen gas or nitrogen gas instead of air as described above.

The acquirer 13 is a device that further acquires biological information of a person who is present in the area 4. Here, examples of the biological information of a person may include body temperature.

For example, an infrared sensor is usable as such an acquirer 13. That is, the infrared sensor is capable of detecting the body temperature serving as the biological information of a person in addition to presence or absence of the person in the area 4.

The acquirer 13 may be substantially the same as the acquirer 3A according to the first embodiment except for the point mentioned above.

The controller 5 controls a hydrogen concentration of the hydrogen-containing gas generated by the hydrogen-containing gas generator 1, on the basis of the biological information of the person acquired by the acquirer 13. For example, a flow rate adjuster (not illustrated) that adjusts a flow rate of air and a flow rate adjuster (not illustrated) that adjusts a flow rate of hydrogen are disposed in the air supply channel 6 and the hydrogen supply channel 9, respectively. The controller 5 may control the hydrogen concentration of the hydrogen-containing gas generated by the hydrogen-containing gas generator 1 by controlling operations of these flow rate adjusters.

In consideration of the stable operation of the hydrogen-containing gas supply system 100, the hydrogen concentration of the hydrogen-containing gas flowing through the hydrogen-containing gas supply channel 8 is desirably set to a value that is below approximately 4% which is the burning limit of hydrogen. However, the hydrogen concentration may be set to 4% or higher in accordance with the operation state and installed environment of the hydrogen-containing gas supply system 100 depending on the circumstance. For example, when a rapid increase in the hydrogen concentration in the area is desired, the hydrogen concentration of the hydrogen-containing gas at an outlet of the hydrogen-containing gas supplier 2 may be set to 4% or higher. In this case, even if the hydrogen concentration of the hydrogen-containing gas is approximately 4% or higher, the concentration of the hydrogen that has flown into the area 4 from the hydrogen-containing gas supplier 2 is quickly decreased by air that is present in the area 4. Thus, no inconvenience may be caused in terms of the stable operation of the hydrogen-containing gas supply system 100 in some cases.

The controller 5 may be substantially the same as the controller 5 according to the first embodiment except for the point mentioned above.

[Operation]

Figure 10:
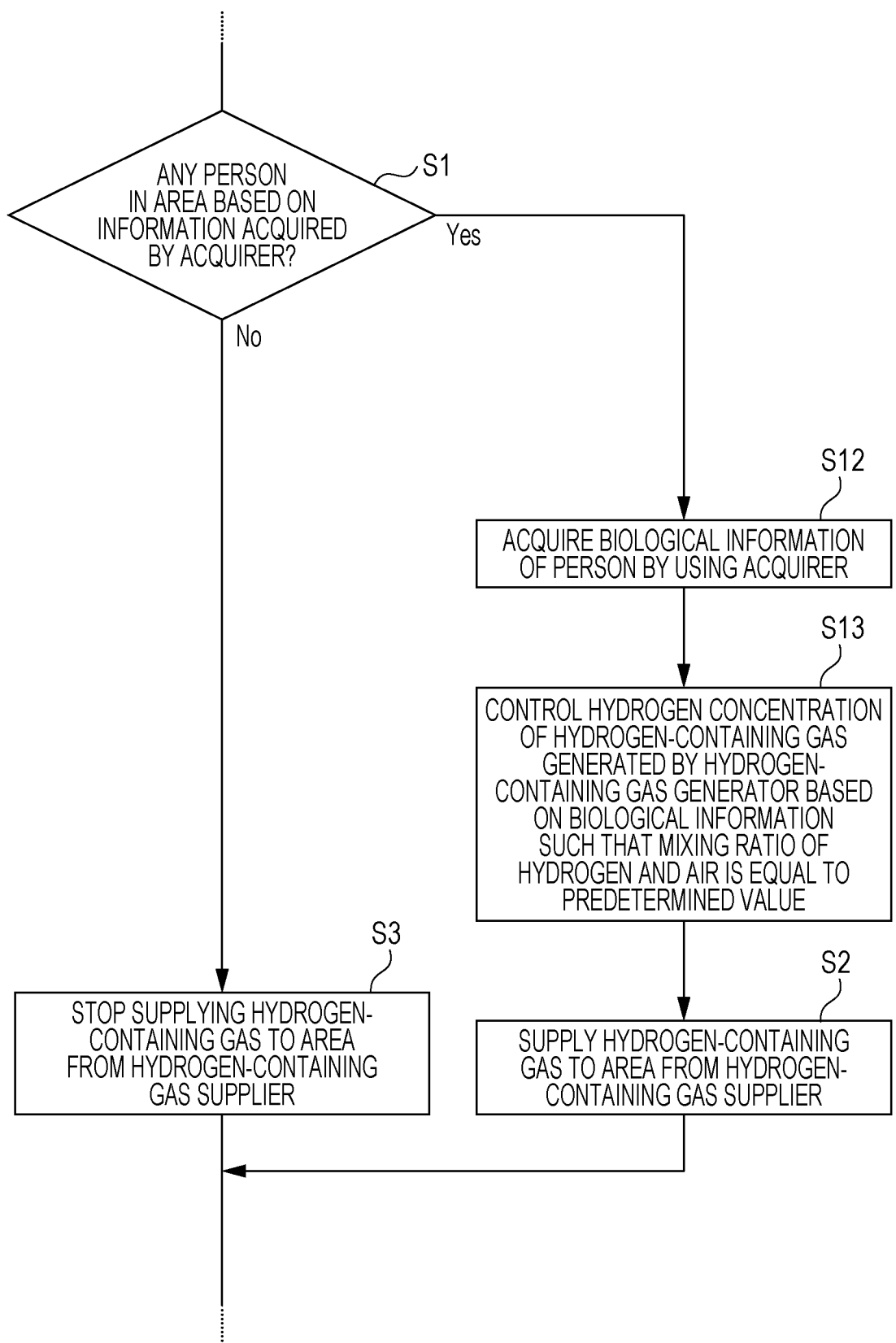
FIG. 10 is a flowchart illustrating an example of an operation of the hydrogen-containing gas supply system according to the third embodiment.

FIG. 10 is a flowchart illustrating an example of an operation of the hydrogen-containing gas supply system according to the third embodiment. The operation described below may be performed by the arithmetic circuitry of the controller 5 in accordance with the control program read from the storage circuitry. However, it is not necessarily mandatory for the controller 5 to perform the operation described below. An operator may perform part or entirety of the operation.

Since steps S1, S2, and S3 of FIG. 10 are substantially the same as steps S1, S2, and S3 of FIG. 4, respectively, a detailed description is omitted.

If it is determined that a person is present in the area 4 on the basis of the information acquired by the acquirer 13 (if "Yes" in step S1), biological information (body temperature, for example) of the person is further acquired by the acquirer 13 (step S12).

Subsequently, in step S13, the hydrogen concentration of the hydrogen-containing gas generated by the hydrogen-containing gas generator 1 is controlled in accordance with the biological information acquired in step S12 such that a mixing ratio of hydrogen and air is equal to a predetermined value. Then, in step S2, the hydrogen-containing gas is supplied to the area 4 from the hydrogen-containing gas supplier 2.

On the other hand, if it is determined that a person is not present in the area 4 on the basis of the information acquired by the acquirer 13 (if "No" in step S1), supplying of the hydrogen-containing gas to the area 4 from the hydrogen-containing gas supplier 2 is stopped (step S3).

As described above, the hydrogen-containing gas supply system 100 according to the present embodiment can appropriately control the hydrogen concentration of the hydrogen-containing gas supplied to the area 4 from the hydrogen-containing gas supplier 2 on the basis of the biological information of the person acquired by the acquirer 13.

For example, it is expected that the higher the body temperature serving as the biological information, the more the generated active oxygen and free radicals in the body. Therefore, in this case, an intake of hydrogen into the body is successfully increased as a result of increasing the hydrogen concentration of the hydrogen-containing gas supplied to the area 4 from the hydrogen-containing gas supplier 2. In this way, the reduction effect of hydrogen against the active oxygen and free radicals in the body is successfully increased.

When the body temperature is low, a situation is expected in which an amount of activity is low and generation of the active oxygen and free radicals in the body is low such as during sleeping, for example. Therefore, in this case, an increase in an amount of hydrogen in the hydrogen-containing gas is successfully suppressed by decreasing the hydrogen concentration of the hydrogen-containing gas supplied to the area 4 from the hydrogen-containing gas supplier 2.

The hydrogen-containing gas supply system 100 according to the present embodiment may be substantially the same as the hydrogen-containing gas supply system 100 according to any of the first embodiment, the example of the first embodiment, the second embodiment, and the first and second modifications of the second embodiment, except for the features mentioned above. That is, the hydrogen-containing gas supply system 100 illustrated in FIG. 1 includes the hydrogen-containing gas generator 1 in FIG. 9. However, the hydrogen-containing gas supply systems 100 illustrated in FIGS. 2, 5, and 7 may include the hydrogen-containing gas generator 1.

(Modification)

While the description has been given of the hydrogen-containing gas supply system 100 according to the third embodiment that appropriately controls the hydrogen concentration of the hydrogen-containing gas supplied to the area 4 from the hydrogen-containing gas supplier 2 on the basis of the biological information of a person acquired by the acquirer 13, the configuration is not limited thereto.

In the hydrogen-containing gas supply system 100 according to the present modification, the controller 5 controls at least one of a supply flow rate or a supply flow velocity of the hydrogen-containing gas supplied to the area 4 from the hydrogen-containing gas supplier 2 on the basis of the biological information of a person acquired by the acquirer 13. For example, the controller 5 may control a supply amount of hydrogen-containing gas supplied to the area 4 from the hydrogen-containing gas supplier 2 by controlling an operation of a not-illustrated pressure booster (fan, for example) included in the hydrogen-containing gas supplier 2.

As described above, the hydrogen-containing gas supply system 100 according to the present modification can appropriately control at least one of a supply flow rate or a supply flow velocity of the hydrogen-containing gas supplied to the area 4 from the hydrogen-containing gas supplier 2 on the basis of the biological information of a person acquired by the acquirer 13.

For example, it is expected that the higher the body temperature serving as the biological information, the more the generated active oxygen and free radicals in the body. Therefore, in this case, an intake of hydrogen into the body is successfully increased by increasing at least one of the supply flow rate or the supply flow velocity of the hydrogen-containing gas supplied to the area 4 from the hydrogen-containing gas supplier 2. In this way, the reduction effect of hydrogen against the active oxygen and free radicals in the body is successfully increased.

When the body temperature is low, a situation is expected in which an amount of activity is low and generation of the active oxygen and free radicals in the body is low such as during sleeping, for example. Therefore, in this case, an increase in an amount of hydrogen-containing gas is successfully suppressed by decreasing the supply amount of hydrogen-containing gas supplied to the area 4 from the hydrogen-containing gas supplier 2.

The hydrogen-containing gas supply system 100 according to the present modification may be substantially the same as the hydrogen-containing gas supply system 100 according to any of the first embodiment, the example of the first embodiment, the second embodiment, and the first and second modifications of the second embodiment, except for the features mentioned above. That is, the hydrogen-containing gas supply system 100 according to the present modification does not necessarily require the hydrogen-containing gas generator 1 illustrated in FIG. 9.

Fourth Embodiment

Figure 11:
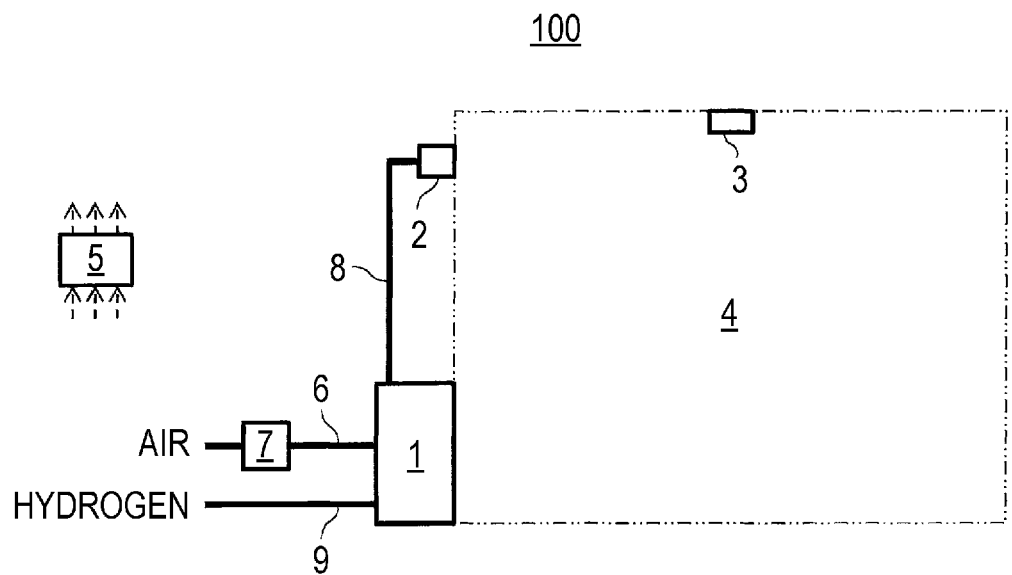
FIG. 11 is a diagram illustrating an example of a hydrogen-containing gas supply system according to a fourth embodiment.

FIG. 11 is a diagram illustrating an example of a hydrogen-containing gas supply system according to a fourth embodiment.

In the example illustrated in FIG. 11, the hydrogen-containing gas supply system 100 includes the hydrogen-containing gas generator 1, the hydrogen-containing gas supplier 2, the acquirer 3, the controller 5, and a filter 7. Since the hydrogen-containing gas supplier 2, the acquirer 3, and the controller 5 are substantially the same as those of the first embodiment, a description is omitted. In addition, the hydrogen-containing gas generator 1 may be substantially the same as the hydrogen-containing gas generator 1 according to the third embodiment except for the point mentioned below.

The filter 7 is a member that removes impurities in air. Specifically, the filter 7 is disposed in the air supply channel 6 coupled to the hydrogen-containing gas generator 1. Impurities such as dust in air flowing through the air supply channel 6 are removed by the filter 7.

The hydrogen-containing gas generator 1 generates a hydrogen-containing gas by mixing hydrogen with air that has passed through the filter 7. That is, the hydrogen-containing gas generator 1 is capable of generating a hydrogen-containing gas of a desired hydrogen concentration by mixing hydrogen from the hydrogen supply channel 9 and air from the filter 7 at a predetermined mixing ratio.

With the configuration above, impurities in air to be mixed with hydrogen can be appropriately removed in the hydrogen-containing gas supply system 100 according to the present embodiment.

The hydrogen-containing gas supply system 100 according to the present embodiment may be substantially the same as the hydrogen-containing gas supply system 100 according to any of the first embodiment, the example of the first embodiment, the second embodiment, the first and second modifications of the second embodiment, the third embodiment, and the modification of the third embodiment, except for the features mentioned above. That is, the hydrogen-containing gas supply system 100 illustrated in FIG. 1 includes the filter 7 and the hydrogen-containing gas generator 1 in FIG. 11. However, the hydrogen-containing gas supply systems 100 illustrated in FIGS. 2, 5, and 7 may include the filter 7 and the hydrogen-containing gas generator 1 or the hydrogen-containing gas supply system 100 illustrated in FIG. 9 may include the filter 7.

Fifth Embodiment

Figure 12:
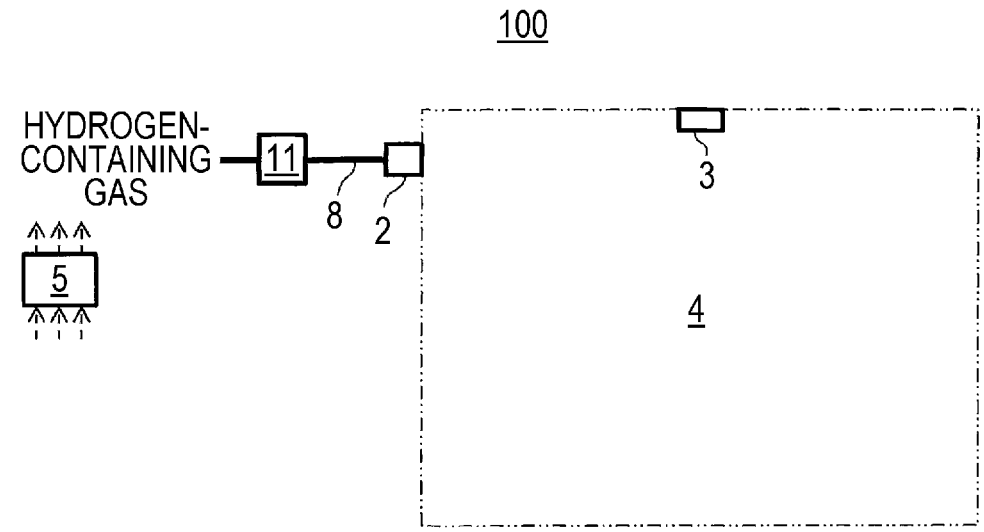
FIG. 12 is a diagram illustrating an example of a hydrogen-containing gas supply system according to a fifth embodiment.

FIG. 12 is a diagram illustrating an example of a hydrogen-containing gas supply system according to a fifth embodiment.

In the example illustrated in FIG. 12, the hydrogen-containing gas supply system 100 includes the hydrogen-containing gas supplier 2, the acquirer 3, the controller 5, and an odorizer 11. Since the acquirer 3 and the controller 5 are substantially the same as those of the first embodiment, a description is omitted. In addition, the hydrogen-containing gas supplier 2 may be substantially the same as the hydrogen-containing gas supplier 2 according to the first embodiment except for the point mentioned below.

The odorizer 11 is a device that adds an odor to a hydrogen-containing gas. In addition, the hydrogen-containing gas supplier 2 is a device that supplies, to the area 4, the hydrogen-containing gas that has passed through the odorizer 11. Specifically, the odorizer 11 is disposed in the hydrogen-containing gas supply channel 8 coupled to the hydrogen-containing gas supplier 2. An odor is added to the odorless hydrogen-containing gas to be supplied to the area 4 from the hydrogen-containing gas supply channel 8.

With the configuration above, the hydrogen-containing gas supply system 100 according to the present embodiment allows a person who is present in the area 4 to easily know that the hydrogen-containing gas is being supplied to the area 4 by the olfactory sense.

The hydrogen-containing gas supply system 100 according to the present embodiment may be substantially the same as the hydrogen-containing gas supply system 100 according to any of the first embodiment, the example of the first embodiment, the second embodiment, the first and second modifications of the second embodiment, the third embodiment, the modification of the third embodiment, and the fourth embodiment, except for the features mentioned above. That is, the hydrogen-containing gas supply system 100 illustrated in FIG. 1 includes the odorizer 11 in FIG. 12. However, the hydrogen-containing gas supply systems 100 illustrated in FIGS. 2, 5, 7, 9 and 11 may include the odorizer 11.

Note that the first embodiment, the example of the first embodiment, the second embodiment, the first and second modifications of the second embodiment, the third embodiment, the modification of the third embodiment, the fourth embodiment, and the fifth embodiment may be combined with one another as long as they do not preclude each other.

In addition, many improvements and other embodiments of the present disclosure are obvious from the description above to persons skilled in the art. Therefore, the description above should be interpreted as mere examples, and are provided so as to teach the best mode for implementing the present disclosure to persons skilled in the art. The details of the structures and/or functions of the present disclosure are substantially changeable without departing from the spirit of the present disclosure.

An aspect of the present disclosure is applicable to a hydrogen-containing gas supply system capable of effectively producing a hydrogen inhale effect stably for a long period while suppressing an increase in an amount of hydrogen used, compared with the related art. In addition, an aspect of the present disclosure is applicable to a hydrogen house including such a hydrogen-containing gas supply system.

What is claimed is:

1. A hydrogen-containing gas supply system comprising:
one or more hydrogen-containing gas suppliers that supply a hydrogen-containing gas to one or more areas in a building;
one or more acquirers that acquire information indicating that a person is present in the one or more areas;
a controller that causes, when it is determined that a person is present in a certain area of the one or more areas in accordance with the information acquired by the one or more acquirers,
at least one of the one or more hydrogen-containing gas suppliers to supply the hydrogen containing gas to the certain area; and
a hydrogen-containing gas generator that generates the hydrogen-containing gas, wherein the one or more acquirers further acquire body temperature information that is biological information of the person who is present in the certain area, and
the controller controls a hydrogen concentration of the hydrogen-containing gas generated by the hydrogen-containing gas generator in accordance with the body temperature information that is the biological information of the person acquired by the one or more acquirers,
wherein the controller causes the one or more hydrogen-containing gas suppliers to increase the hydrogen concentration of the hydrogen-containing gas supplied to the area, as body temperature serving as the biological information acquired by the one or more acquirers increases, or
wherein the controller causes the one or more hydrogen-containing gas suppliers to decrease at least one of the hydrogen-concentration of the hydrogen-containing gas supplied to the area when body temperature serving as the biological information acquired by the one or more acquirers decreases.

2. The hydrogen-containing gas supply system according to claim 1, wherein the one or more acquirers are disposed in the one or more areas.

3. The hydrogen-containing gas supply system according to claim 1, wherein the controller causes at least one of the one or more hydrogen-containing gas suppliers to supply the hydrogen-containing gas to the certain area when it is determined that a person is present in the certain area in accordance with the information acquired by the one or more acquirers from an information terminal.

4. The hydrogen-containing gas supply system according to claim 1, wherein
the one or more hydrogen-containing gas suppliers are a plurality of hydrogen-containing gas suppliers each of which supplies the hydrogen-containing gas to a corresponding one of a plurality of areas,
the one or more acquirers are a plurality of acquirers each disposed in a corresponding one of the plurality of areas, and
the controller causes, when a certain acquirer among the plurality of acquirers acquires information indicating that a person is present in the certain area and when it is determined that the person is present in the certain area in accordance with the information acquired by the certain acquirer, at least one of the one or more hydrogen-containing gas suppliers to supply the hydrogen-containing gas to the certain area.

5. The hydrogen-containing gas supply system according to claim 1, wherein
each of the one or more acquirers is a first detector that detects that a person is present in the certain area, and
upon the first detector detecting that a person is present in the certain area,
the controller causes the one or more hydrogen-containing gas suppliers to operate.

6. The hydrogen-containing gas supply system according to claim 1, wherein
each of the one or more acquirers is a second detector that detects information indicating a position where a person is present in the certain area, and
upon the second detector detecting the information indicating the position where the person is present, the controller causes at least one of the one or more hydrogen-containing gas suppliers to supply the hydrogen-containing gas toward the position.

7. The hydrogen-containing gas supply system according to claim 1, wherein
   each of the one or more acquirers is a second detector that detects a position where a person is present in the certain area, and
   the controller causes at least one of the one or more hydrogen-containing gas suppliers to control at least one of a supply flow rate or a supply flow velocity of the hydrogen-containing gas in accordance with the position where the person is present and that is detected by the second detector.

8. The hydrogen-containing gas supply system according to claim 1, wherein
   the one or more acquirers further acquire biological information of the person who is present in the certain area, and
   the controller causes at least one of the one or more hydrogen-containing gas suppliers to control at least one of a supply flow rate or a supply flow velocity of the hydrogen-containing gas in accordance with the biological information of the person acquired by the one or more acquirers.

9. The hydrogen-containing gas supply system according to claim 1, further comprising:
   a filter that removes impurities in air; and
   a hydrogen-containing gas generator that generates the hydrogen-containing gas by mixing hydrogen with the air having passed through the filter.

10. The hydrogen-containing gas supply system according to claim 1, further comprising
    an odorizer that adds an odor to the hydrogen-containing gas, wherein
    the one or more hydrogen-containing gas suppliers supplies to the certain area the hydrogen-containing gas having passed through the odorizer.

11. A hydrogen house comprising the hydrogen-containing gas supply system according to claim 1.

\* \* \* \* \*